United States Patent
Hobby et al.

(10) Patent No.: US 6,246,227 B1
(45) Date of Patent: Jun. 12, 2001

(54) SENSOR FOR MEASURING THE MAGNETIC CHARACTERISTICS OF A GAS

(76) Inventors: James Hobby, 7 Bridger Way, Crowborough, East Sussex, TN6 2XD; Danny Holman, Jamais Finis, Hurtis Hill, Crowborough, East Sussex TN6 3AF; Riad Mouhamed Adel Kocache, Amani, 3 Courtlands Place, Crowborough, East Sussex TN6 1JJ, all of (GB)

( * ) Notice: Subject to any disclaimer, the term of this patent is extended or adjusted under 35 U.S.C. 154(b) by 0 days.

(21) Appl. No.: 09/219,514

(22) Filed: Dec. 23, 1998

(30) Foreign Application Priority Data

Dec. 24, 1997 (GB) .................................................... 9727306

(51) Int. Cl.⁷ ............................. G01N 27/74; G01R 33/12
(52) U.S. Cl. .......................... 324/204; 324/201; 73/25.02
(58) Field of Search .................................... 324/201, 204; 73/25.02

(56) References Cited

U.S. PATENT DOCUMENTS

| | | | |
|---|---|---|---|
| 2,744,234 | * 5/1956 | Munday et al. | 324/204 |
| 3,815,018 | * 6/1974 | Gast et al. | 324/201 |
| 3,826,974 | * 7/1974 | Kocache et al. | 324/201 |
| 4,983,913 | * 1/1991 | Krause et al. | 324/204 |
| 5,369,980 | * 12/1994 | Kocache | 324/204 X |
| 5,932,794 | * 8/1999 | Fabinski et al. | 324/204 X |

FOREIGN PATENT DOCUMENTS 1 220 413   1/1971   (GB) .

OTHER PUBLICATIONS

International Publication No. WO 92/05436, dated Apr. 2, 1992, by Riad Kocache.

* cited by examiner

Primary Examiner—Gerard R. Strecker
(74) Attorney, Agent, or Firm—Dykema Gossett PLLC

(57) ABSTRACT

A gas measurement cell has a measurement element suspended to oscillate about a suspension axis in a magnetic field. A coil which oscillates with the element may have electrical signals applied to it to initiate oscillation and also provides an output whereby the frequency of oscillation can be measured.

8 Claims, 4 Drawing Sheets

SENSOR FOR MEASURING THE MAGNETIC CHARACTERISTICS OF A GAS

BACKGROUND OF THE INVENTION

1. Field of the Invention

The present invention relates to apparatus for the measurement of the quantity of oxygen, or other relatively strong paramagnetic gas, in a gaseous mixture by use of its magnetic susceptibility through its effect on the induced motion of a test body in a magnetic field.

2. The Prior Art

The measurement of oxygen via its paramagnetic susceptibility has been known since the middle of the $19^{th}$ century when Faraday showed that all materials interacted with a magnetic field. Gases were found in general to be repelled by a magnetic field and we described as being diamagnetic, whilst oxygen and some other gases were found to be attracted to a magnetic field and called paramagnetic. The very high paramagnetism of oxygen enabled its measurement by magnetic susceptibility techniques.

Two principal methods were originally developed for implementation of this technique. One was to employ a uniform magnetic field whilst the other employed the non-uniform field as originally described by Faraday. An example of the former technique is given by L. G. Gouy in Compt. Rend. Vol. 109 (1885) 935 while an example of the latter is given by P. W. Selwood in Magnetometry 2nd Edition, 1993, Interscience N/Y London 1956. The bulky and delicate nature of these instruments led to the development of further apparatus amongst which the most successful were those based on the original Faraday gas susceptibility balance. In these designs a test body of well defined shape is suspended inside a gas cell. The test body is made of materials, such as quartz, which have a low value of diamagnetic susceptibility and is suspended such that a strong non-uniform magnetic field is present across it. When the paramagnetic gas enters the test cell the gas tends to move to congregate at the point of strongest magnetic field causing a change in the position of the test body which can be measured and related to the concentration of paramagnetic gas in the cell.

Several forms of test body have been investigated including the commonly used dumbbell (e.g. G. C. Haven, Physical Review Vol. 41 (1932) 337) and also with modifications using a flattened structure (e.g. U.S. Pat. No. 3,815,018). Some other patents using dumbbell based designs for Faraday balances include U.S. Pat. No. 2,416,344 and U.S. Pat. No. 2,962,656. The apparatus described by these and other patents are similar in that all of them employ an optical method to detect the rotation of the dumbbell as the magnetic nature of the gas in the test cell is altered. Although in some cases a feedback system was employed in order to produce a null balance system, by electromagnetism, by electrostatic means (U.S. Pat. No. 3,026,472) and by variation of the magnetic field (U.S. Pat. No. 3,879,658) all of these techniques still required the use of optical means to provide the final measurement.

Non optical detection systems have also been disclosed that employ extra components to detect the rotation of the test body. These include the use of magneto-resistive pickup (GB-A-1 220 413), employment of separate high frequency excitation and pickup coils (U.S. Pat. No. 3,714,557), and capacitive sensing of the rotation, (U.S. Pat. No. 3,612,991). In these cases the use of an optical detection method has been replaced by the use of an alternative but in each case the new measurement technique is an additional system to the basic susceptibility balance and acts as an alternative to the optics.

WO92/05436 described an alternative arrangement for the measurement of the proportion of a paramagnetic gas not requiring the additional detection system extra to the basic susceptibility balance. In particular, it proposed that a test element should be made to vibrate in a varying magnetic field by the application of a current through the test element and where the electrical conductors used to apply the current to cause the current to cause oscillation were also used to sense the subsequent oscillation of the elements in the magnetic field. As described in that document, certain parameters of the oscillation, such as damping and frequency, are dependent on the proportion of the paramagnetic gas in the cell and therefore this proportion can be determined from measurements of the ongoing oscillation.

SUMMARY OF THE INVENTION

The present invention provides apparatus for the measurement of the proportion of paramagnetic gas in a gas mixture comprising a chamber to which said gas mixture may be admitted, means arrange to generate, within such chamber, a gradient magnetic field, a test element and means arranged to mount said test element in said gradient magnetic field such that the test element may rotationally oscillate about an axis, wherein said mounting means comprises electrical conductor means arranged to carry current to and from said test element whereby current may be applied to said test element to cause oscillation thereof and whereby EMF generated by movement of the test element in said gradient magnetic field may be measured.

The present invention therefore advantageously provides a gas sensor cell of simple construction in that there is no need to provide additional sensing elements to monitor the movement of the test element. This is because the same conductors which pass the current to cause the oscillation of the test element are used as the input to a sensing means which, by way of the generated EMF, can determine the characteristics of the oscillation of the element. From the variation in these characteristics the proportion of paramagnetic gas in the cell may be determined.

The present invention therefore utilizes principles set out in WO 92/05436, but has the advantage of using, in the preferred embodiment, well known gas sensor elements in its construction and also the number of degrees of freedom of movement of the test element is limited which considerably simplifies the required driving and sensing circuitry.

BRIEF DESCRIPTION OF THE DRAWINGS

The present invention will be better understood from the following description of a preferred embodiment given by way of example and with reference to the accompanying drawings, in which.

DETAILED DESCRIPTION OF THE DRAWINGS

In general terms, in the invention a gas measurement cell has a measurement element suspended to oscillate about a suspension axis in a magnetic field. A coil which oscillates with the element may have electrical signals applied to it to initiate oscillation and also provides an output whereby the frequency of oscillation can be measured.

In general terms, the invention employs a test body suspended in a magnetic field to determine the paramagnetic portion of a mixture of gases using the electrical element in the test body as the active component in the measurement.

Figure 2A:
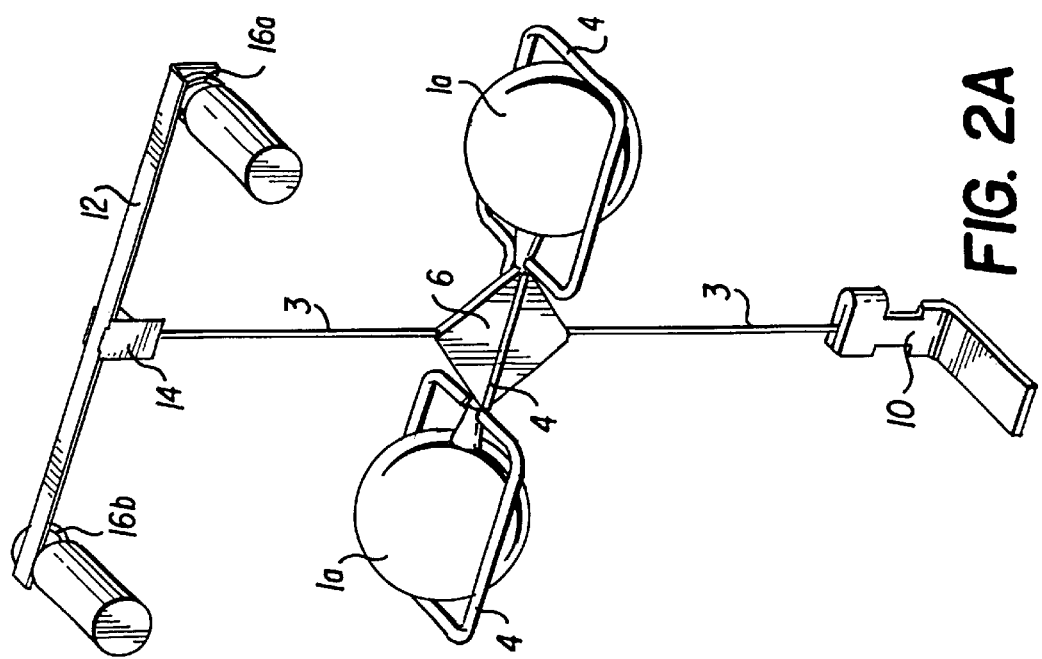
FIGS. 2A and 2B show one preferred arrangement for mounting the dumbbell in the sensor cell.
Figure 1:
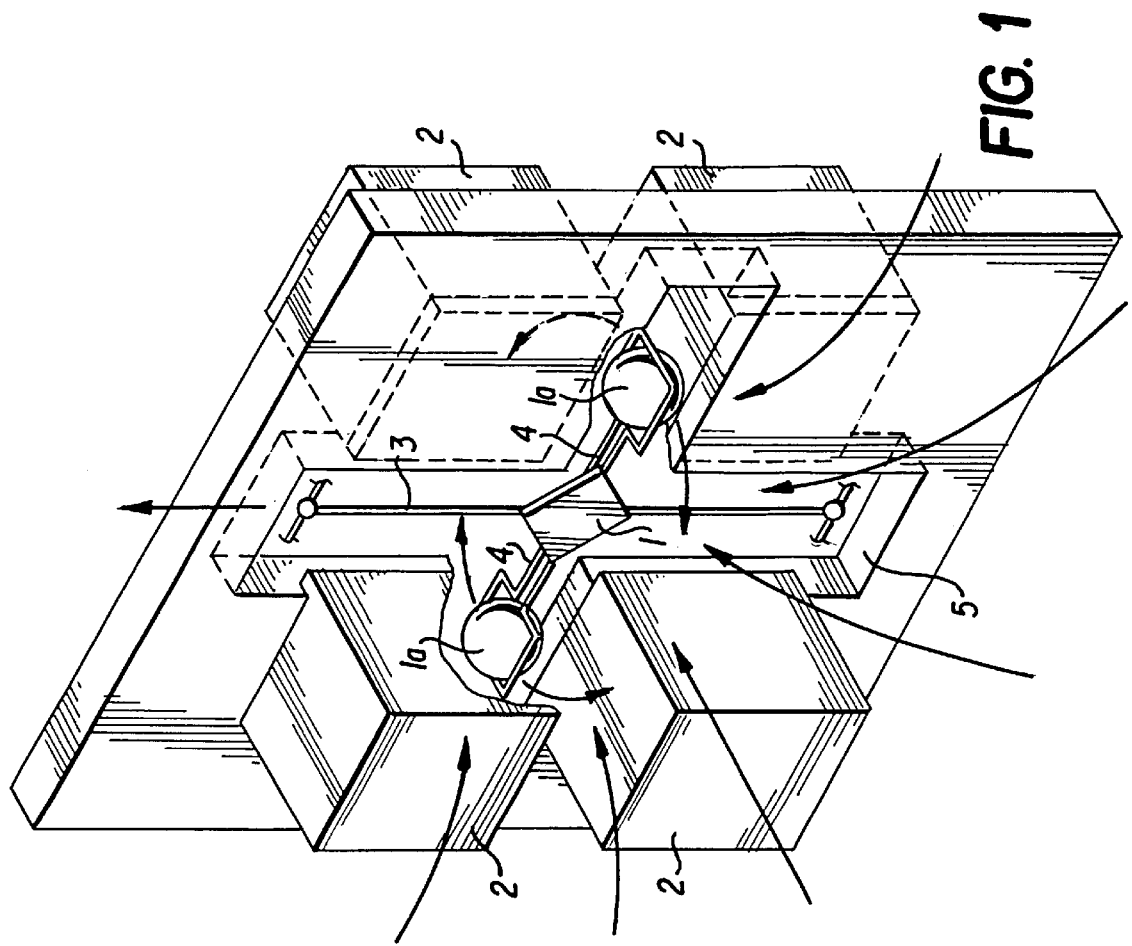
FIG. 1 is a schematic illustration of a gas sensor cell according to the preferred embodiment.
Figure 2B:
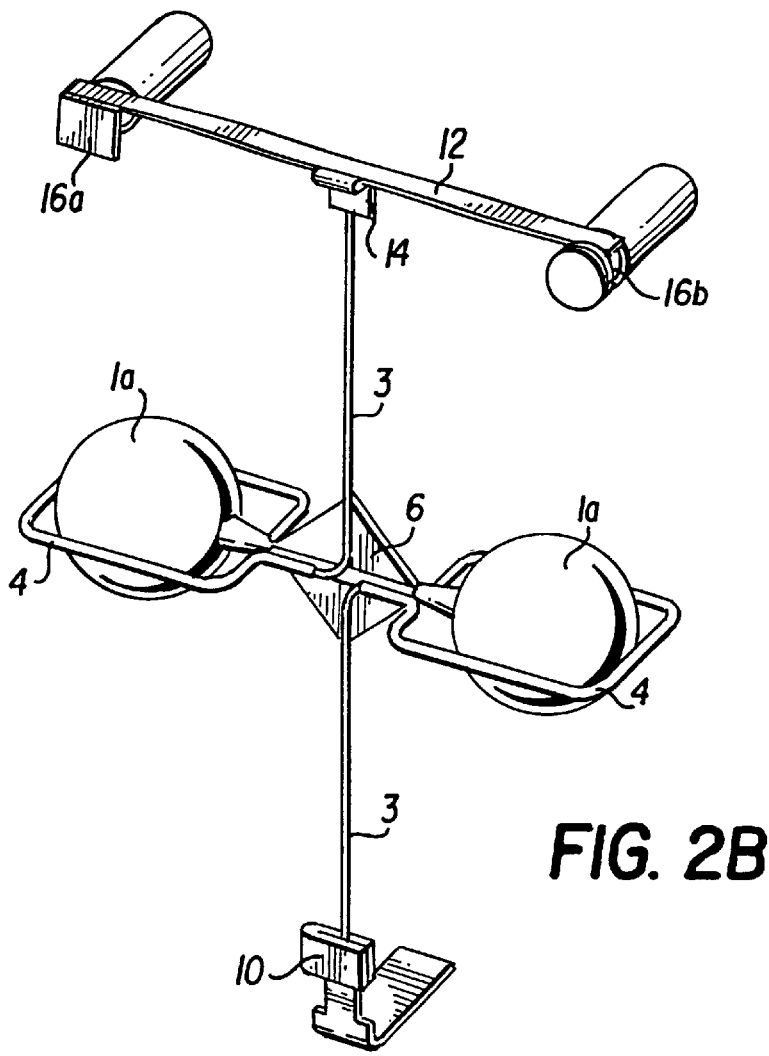

More particularly the apparatus described herein allows for the measurement of the effect of variation in a gas sample's susceptibility on a test body 1 suspended within a non-uniform magnetic field without the use of either optical sensors or additional detector components. Referring to FIG. 1, test body 1 is in the form of a dumbbell and comprises two spheres 1a made from materials of low magnetic susceptibility. The test body is suspended in a strong non-uniform magnetic field produced by the magnets 2 by a strip of known torque constant 3. The strip 3 is joined to the test body 1 such that it connects to a single turn of an electrical conductor (a coil) 4 around the test body as shown in FIGS. 2A and 2B. The whole of this assembly is mounted in a gas chamber 5 to allow control of the gases presented to the apparatus.

In operation a drive signal is supplied to the dumbbell 1 via the strip 3 to the coil 4. This signal may be either continuous or pulsed but is set so as to cause the electromagnetic forces generated between the current in the coil and the non-uniform magnetic field to cause the dumbbell to start rotating around an axis defined by supporting strip 3. The magnitude of the excitation is set so as to cause the rotation to stay well within the linear torque value range of the strip which is typically less than a 50° degree arc. As a result of the magnetic field a force is applied to the dumbbell whose magnitude can be calculated by:

$$F = H\frac{dH}{dx}V(X_o - X_S) \quad (1)$$

where F is the force, H the magnetic field strength, dH/dx is the gradient of the magnetic field strength, V the volume, $X_0$, the magnetic susceptibility of the test body and $X_s$ the susceptibility of the gas surrounding the dumbbell.

The natural frequency of the suspension is described by:

$$f = \frac{1}{2\pi\sqrt{I\frac{L}{K}}} \quad (2)$$

where f is the frequency of oscillation, I is the rotational inertia of the system, L is the effective length of the mounting strip and K is the restoring torque value, which is a combination of the torque value of strip 3 and the force generated according to equation 1.

When the gas surrounding the dumbbell is changed from a weak diamagnetic gas, e.g. nitrogen, to a paramagnetic one, e.g. an oxygen mixture, the value of $X_s$ in equation 1 alters, thus altering the force applied to the test element. This causes an alteration in the rest position of the test element. Further, this causes an alteration in the value of K in equation 2, in turn causing the natural frequency of the suspension to change. These two effects are additive in terms of the frequency shift. Referring to equation 2 above, the values of I and L are known parameters of the system in question, and accordingly, on measuring the value of f, the value of K can be established as:

$$K = 4ILπ^2 f^2 \quad (3)$$

As mentioned above, K is a combination of the torque value of strip 3 and the force f generated by equation 1. The exact relationship between K and f is therefore a function of the apparatus and can be either empirically measured or theoretically determined. It can therefore be taken that:

$$F=f(K) \quad (4)$$

Where "f" is a function which represents the established relationship between F and K. Referring then to equation 1 above, the values of X,H, dH/dx and V are again known parameters of the system in question and accordingly, combining equations 1 and 4, the value of $X_s$ can be determined:

$$X_s = X_0 - \frac{f(K)}{HVdH/d_x} \quad (5)$$

From the value of $X_s$, the proportion of paramagnetic, oxygen gas can be calculated in a conventional fashion.

The coil 4 is used both to induce the rotational motion, when driven with a suitable electrical signal, as described above and to detect the said motion by using the EMF induced into the coil as it sweeps through the magnetic field. As the magnitude of the EMF is proportional to the equivalent frequency of rotation of the dumbbell it can be seen from the above that a measurement of the sample's magnetic susceptibility can be obtained without the use of optical or other independent measurement components.

The signal used to induce motion of the dumbbell may either be continuous or a finite period repetitive one. The signal generated by the system may then be detected by either: 1) changes in frequency (such as if the device is driven by a free running oscillator); 2) amplitude (such as when the device is driven with fixed frequency pulses and the coupling of a signal to induce motion that will be proportional to the frequency difference between that of the source and the dumbbell; 3) shape (comparing a reference signal with that produced by the sensor; or 4) any method by which an AC electrical signal may be compared to another.

Figure 3:
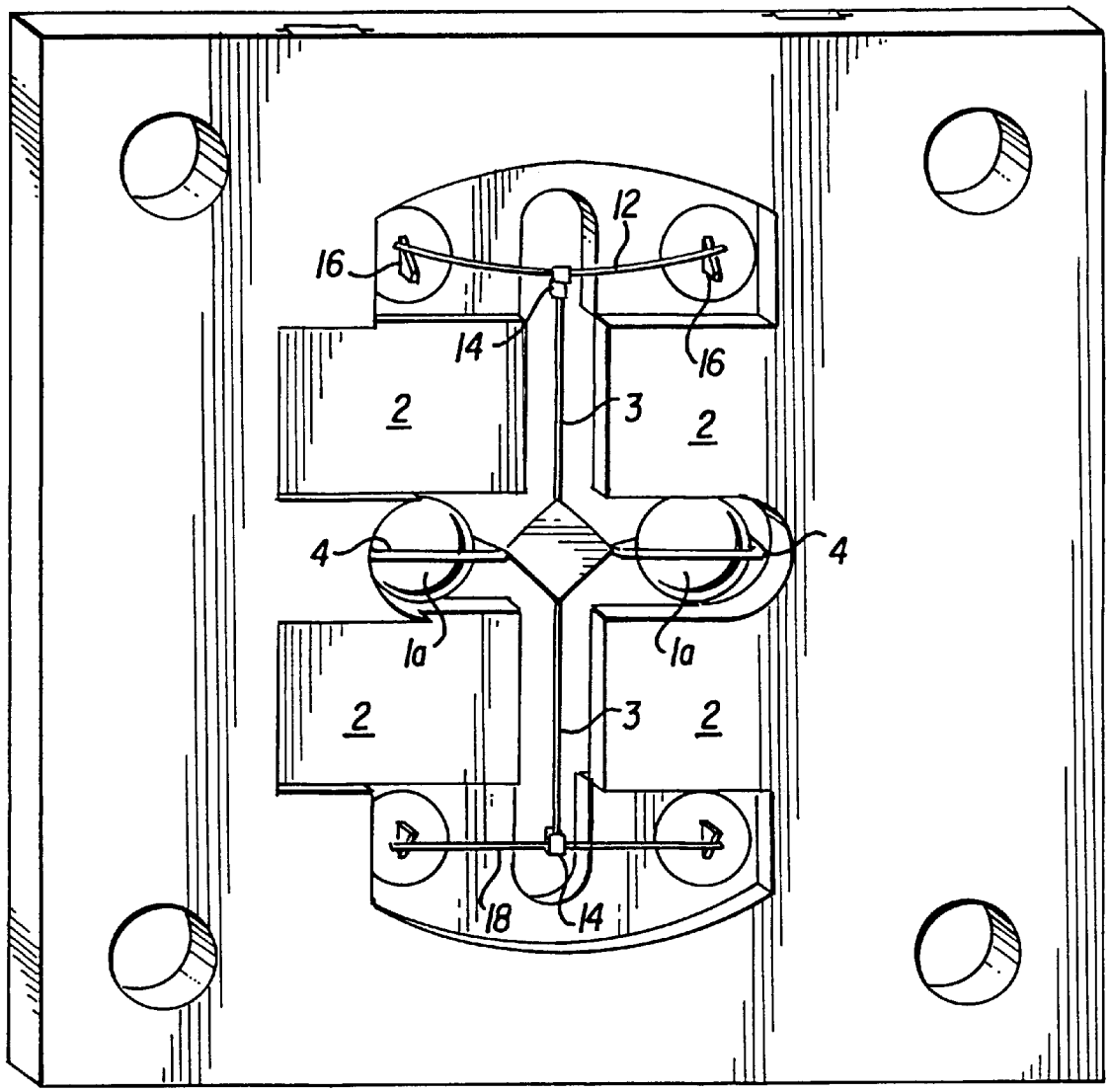
FIG. 3 shows an alternative mounting arrangement.

FIGS. 2A and 2B and 3 illustrate particularly preferred mounting arrangements for the dumbbell shown in FIG. 1 in which corresponding reference numerals to those used in FIG. 1 identify corresponding parts and which are discussed in more detail in the following.

In FIGS. 2A and 2B, which shows front and rear views respectively of one preferred mounting arrangement, dumbbell 1 is mounted as before, by strips 3 attached to central element 6, on which spheres 1a are mounted. Central element 6 is simply a structured part. One of strips 3 is attached to fixed mounting element 10.

The other of strips 3 is fixed to a central point of flexible spring 12 by way of mounting element 14. This arrangement enables changes in dimensions which arise with temperature variation due to differences in thermal expansion coefficients between the materials of the frame, dumbbell and mounting strip to be accommodated. In particular, flexing of spring 12 allows such changes to occur without the position of the dumbbell in the magnetic field changing substantially and while maintaining any required tension in strip 3.

The position of the dumbbell in the field significantly affects the behaviour of the sensor and therefore it is important that it be maintained. While it may be possible to match the temperature coefficients of the various materials, the arrangement described above is considerably more simple.

The spring 12 is mounted at positions 16a, 16b. In the arrangement of FIGS. 2A and 2B, the spring is fixed to mount 16a while simply resting against mount 16b such that it is permitted to flex as required.

FIG. 3 shows a further alternative mounting arrangement in a cell. As in FIGS. 2A and 2B, one of the strips 3 is mounted to a flexible spring 12, but in this case the fixed mounting of the other of strip 3 is by way of a fisher mounting 14 to fixed bar 18. This enables each end of strips 3 to be fixed using the same form of mounting element 14, a preferred form of which will be discussed below.

In a further alternative, fixed bar 18 in FIG. 3 may be replaced by a second spring 12 so as to provide an entirely symmetrical mounting arrangement for the test body.

Figure 4:
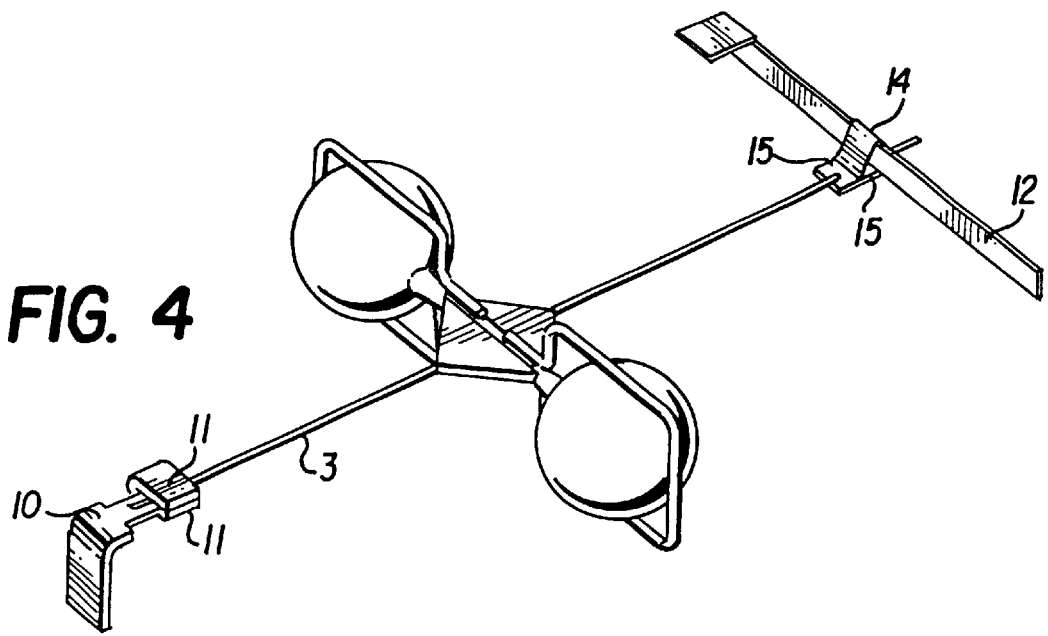
FIG. 4 illustrates the attachment of the mounting strip to the mounting elements.

FIG. 4 illustrates in more detail the attachment of mounting elements such as elements 10 and 14, to the strips 3, in the arrangement of FIGS. 2A and 2B. Mounting element 10 is provided with two flat portions 11. The mounting strip 3 passes between two flat parts 11 of mounting element 10 and passes out beyond them. Correspondingly element 14 has two flat portions 15 between which strip 3 passes. The strip 3 can then be pulled to set the tension correctly and then finally fixed by welding together the two flat parts of each mounting element with the strip between.

Such a sandwich weld has considerable advantages over simply welding the strip to one face of the flat parts. The thickness of the strip 3 is typically of the order of several $\mu$m while the thickness of the flat parts may be tens of hundreds of $\mu$m. The welding of two such differently sized pieces is difficult without heat damaging the thinner strip. The use of the sandwich form as illustrated reduces such problems and also ensures that any heat damaged portion of the strip is within the joint. This ensures that the portion of the ship which is part of the twisting motion of the sensor is not heat damaged.

Preferably, for instance in mounting the strip to spring 12 the mount 14 is made integrally with the spring 12 and the flat parts 15 of the joint 14 are formed as flaps on spring 12 and folded as necessary to form mount 14.

Figure 5:
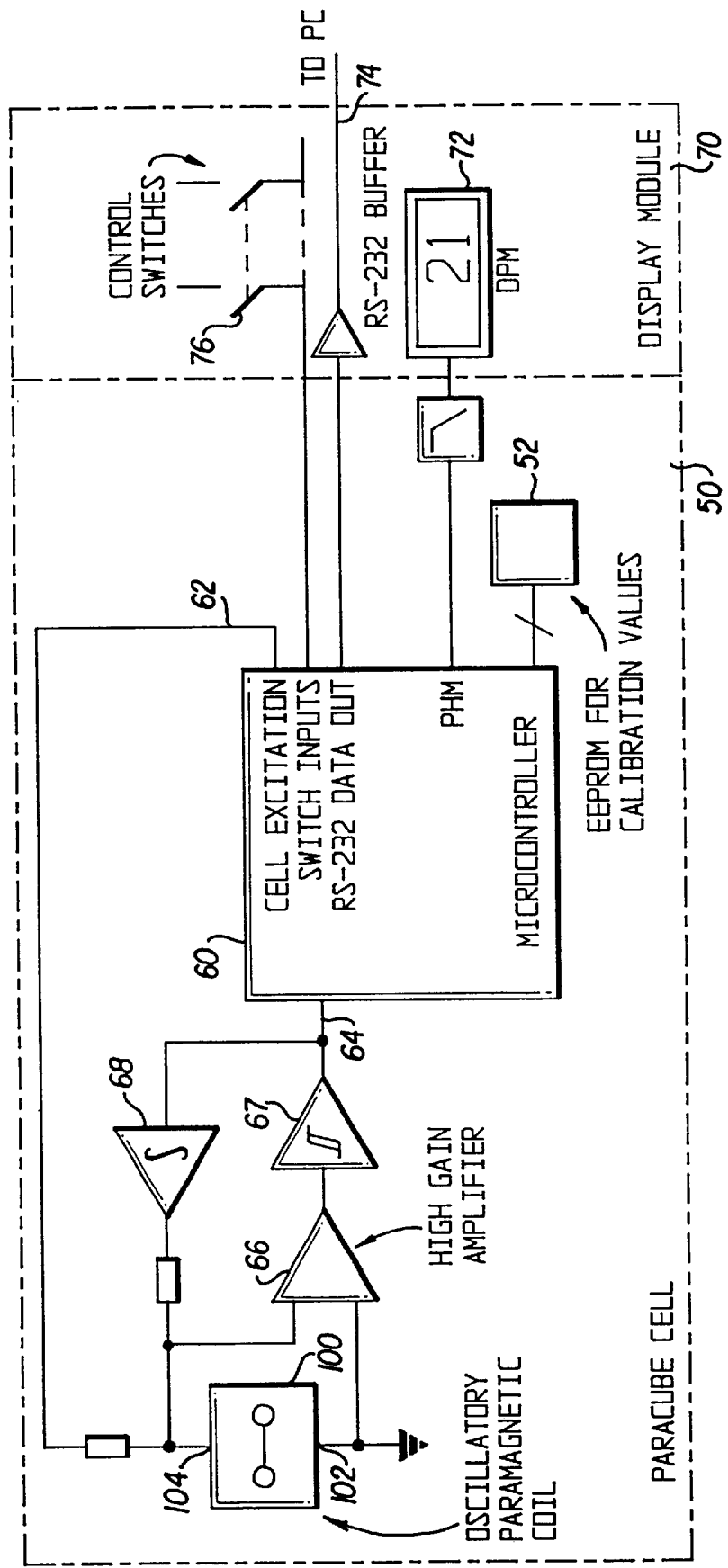
FIG. 5 is a schematic representation of apparatus utilizing the gas sensor cell of FIG. 1.

FIG. 5 is a schematic diagram illustrating one possible way in which the cell described above may be incorporated into complete apparatus which measures the paramagnetic gas proportion in a gas sample as mentioned above. The apparatus illustrated in FIG. 5 can be considered in two sections, a measurement section 50 and an input/output section 70.

Measurement section principally comprises a gas cell 100 of the type described in detail above and a microcontroller 60. Microcontroller 60 controls the electrical operation of cell 100, while the gas to be analysed is passed through the measurement chamber in a well known manner. Cell 100 simply has two electrical connections which connect to respective ends of strip 3. As described above, by way of these two connections, the operation of the cell may be driven and also sensed. As illustrated, one of the connections 102 is simply connected to ground.

In order to excite the cell 100, a suitable input, such as a pulse, is applied to connection 104 by the microcontroller 60, by way of connection 62. The ensuing oscillating output is applied to input 64 of microcontroller 60 by way of amplifier 66 and signal conditioning means 67, which are provided with appropriate feedback means 68. The signal is conditioned such that the signal input at input 64 is of a generally square profile such that microcontroller 60 can easily work with the signal.

According to one mode of operation, when the system is switched on a number of pulses are applied to cell 100 in order to cause the dumbbell to oscillate. Subsequently, in order to track and maintain the oscillation of the dumbbell, the time after the application of each pulse until the next zero crossing at input 64 is measured, and pulses are applied at the rate of once per cycle to maintain the oscillation. When the natural frequency of oscillation changes as a result of changes in the gas mixture, this affects the measured time to the zero crossing and hence such changes are tracked by the microcontroller 20. In this way, the natural oscillation frequency f mentioned above is measured by microcontroller 20.

As discussed in relation to equations (1)–(5), in addition to the value of f it is also necessary to know other system parameters in order to perform the appropriate calculations. In the arrangement illustrated in FIG. 5 there is provided a memory device 52, for instance in the form of an EEPROM, which has stored in it the values of the cell characteristics discussed above. Given these, and the measured value of f, microcontroller 20 calculates the value of $X_s$ in accordance with equation (5). As is well known, this gives a direct measure of the proportion of oxygen, or other paramagnetic gas, present in the gas mixture being measured.

As mentioned above, the apparatus in FIG. 5 also includes an input/output section 70. In its simplest form this comprises a display means 72 which gives a visual display for example of the proportion of oxygen as determined by the microcontroller 20. Additionally, the input/output section 70 may provide for a communications link 74, e.g. an RS 232 connection, to enable data to be provided to a suitable computer such as a PC. As illustrated, input/output section 70 also includes switch means 76 which control the operation of the device.

As illustrated, FIG. 5 is simply one exemplary form of control for the cell described in detail above, and many variations are possible.

What is claimed is:

1. An apparatus for the measurement of the magnetic characteristics of a gas comprising:
   a chamber to which said gas may be admitted,
   means arranged to generate, within said chamber, a gradient magnetic field,
   a test element comprising material of known magnetic susceptibility and a conductive path, and
   mounting means arranged to mount the test element in said gradient magnetic field such that the test element may rotationally oscillate about an axis,
   wherein said mounting means comprises electrical conductor means arranged to carry current to and from said conductive path whereby current may be applied to said conductive path to cause oscillation of said test element and whereby EMF generated in said conductive path by movement of the test element in said gradient magnetic field may be measured, and
   wherein the movement represented by said measured EMF provides said measurement of the magnetic characteristics of the gas.

2. The apparatus according to claim 1 in which said test element is in the form of a dumbbell.

3. The apparatus according to claim 1 in which said test element comprises an electrical loop or coil in electrical connection with said mounting means.

4. The apparatus according to claim 1 further comprising calculation means arranged to determine, from said EMF and changes therein, a frequency of oscillation of said test element.

5. The apparatus according to claim 4 further comprising means to calculate, from said frequency, the magnetic susceptibility of said gas.

6. The apparatus according to claim 1 in which said mounting means comprises two electrically conductive strips extending from said test element in mutually opposite directions substantially along said axis and which are mounted at their ends distal from said test element to respective mounting elements.

7. The apparatus according to claim 6 in which at least one of said mounting elements comprises resilient means arranged to maintain a predetermined tension in said electrically conductive strips.

8. The apparatus according to claim 7, in which said resilient means comprises a spring strip positioned substantially perpendicular to said axis.

* * * * *